United States Patent [19]
Fraiser et al.

[11] Patent Number: 5,648,211
[45] Date of Patent: Jul. 15, 1997

[54] STRAND DISPLACEMENT AMPLIFICATION USING THERMOPHILIC ENZYMES

[75] Inventors: Melinda S. Fraiser, Durham; Catherine A. Spargo, Cary; George Terrance Walker, Chapel Hill, all of N.C.; Mark Van Cleve, San Jose, Calif.; David James Wright, Chapel Hill, N.C.; Michael C. Little, Baltimore, Md.

[73] Assignee: Becton, Dickinson and Company, Franklin Lakes, N.J.

[21] Appl. No.: 229,279

[22] Filed: Apr. 18, 1994

[51] Int. Cl.$^6$ ............................... C12Q 1/68; C12P 19/34
[52] U.S. Cl. ................................................. 435/6; 435/91.2
[58] Field of Search ........................... 435/5, 6, 91.2; 935/77, 78

[56] References Cited

U.S. PATENT DOCUMENTS

| | | | |
|---|---|---|---|
| 5,192,674 | 3/1993 | Oshima et al. | 435/194 |
| 5,270,184 | 12/1993 | Walker et al. | 435/91.2 |

FOREIGN PATENT DOCUMENTS

| | | |
|---|---|---|
| 0 497 272 A1 | 8/1992 | European Pat. Off. . |
| 0 517 418 A2 | 12/1992 | European Pat. Off. . |
| WO91/09944 | 7/1991 | WIPO . |
| WO91/09950 | 7/1991 | WIPO . |
| WO92/018130 | 2/1992 | WIPO . |
| WO92/06202 | 4/1992 | WIPO . |
| WO92/05287 | 4/1992 | WIPO . |
| WO92/06200 | 4/1992 | WIPO . |
| WO92/09689 | 6/1992 | WIPO . |
| WO93/25691 | 12/1993 | WIPO . |

OTHER PUBLICATIONS

Walker, G. T. "Empirical aspects of strand displacement" PCR Methods and Applications 3:1–6 (1993).

T. Uemori, et al. "CLoning of the DNA Polymerase Gene of *Bacillus caldotenax* and Characterization of the Gene Product" *J. Biochem.* 113, 401–410 (1993).

Y. Shengyu, et al. "Heat Stable DNA Polymerase I Large Fragment Resolves Hairpin Structure in DNA Sequencing" *Scientia Sinica* 30, 503–506 (1987).

T. Uemori, et al. "Organization and nucleotide sequence of the DNA polymerase gene from the archaeon *Pyrococcus furiosus*" *Nucl. Acids Res.* 21, 259–265 (1993).

J. A. Burrows, et al. "Purification and properties of DNA polymerase from *Bacillus caldotenax*" *Biochem. J.* 287, 971–977 (1992).

H. Kong, et al. "Characterization of a DNA Polymerase from the Hyperthermophile Archaea *Thermococcus litoralis*" *J. Biol. Chem.* 268, 1965–1975 (1993).

Bio–Rad Catalogue (1993) p. 186.

New England Biolabs (1992) p. 23.

Wang et al, J. Biol. Chem 264:1163–1171 (1989).

Longo et al, Gene 93:125–128 (1990).

*Primary Examiner*—Stephanie W. Zitomer
*Assistant Examiner*—Eggerton Campbell
*Attorney, Agent, or Firm*—Donna R. Fugit

[57] ABSTRACT

Strand Displacement Amplification methods (thermophilic SDA) which can be performed over a broad temperature range (37° C. to 70° C.). The preferred temperature range for thermophilic SDA is 50° C. to 70° C. It has been found that certain thermophilic restriction endonucleases are capable of nicking the hemimodified restriction endonuclease recognition/cleavage site as required by SDA and dissociating from the site. It has further been found that certain thermophilic polymerases are capable of extending from the nick while displacing the downstream strand. Thermophilic SDA, because of reaction temperatures higher than previously possible with conventional SDA enzyme systems, has improved specificity and efficiency, reduced nonspecific background amplification, and potentially improved yields of amplification products. In addition, the need to add the enzymes in a separate step after the initial heat denaturation of double stranded targets is eliminated when enzymes capable of tolerating the denaturation temperature are used.

18 Claims, 2 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

GCGGATCCGG CCGAGT                                                16

( 2 ) INFORMATION FOR SEQ ID NO:2:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

```
CACTTGATGC CTCCGTGTAA G                                    21
```

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
TACAATAGTC CCAATCTACC CGAGCTTACA CGGAGGCATC AAGTG          45
```

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TACAATAGTC CCAATCTACT CGGGCTTACA CGGAGGCATC AAGTG          45
```

( 2 ) INFORMATION FOR SEQ ID NO:5:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CCGGAATTCG AATGCCAAAA GACTGGGTCT CCAGGAACCA ACTCGGCCGG ATCCGC    56
```

( 2 ) INFORMATION FOR SEQ ID NO:6:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CCGGAATTCT GGTTCCTGGA GACCCAGTCT TTTGGCATTC ACTCGGCCGG ATCCGC    56
```

( 2 ) INFORMATION FOR SEQ ID NO:7:

( i ) SEQUENCE CHARACTERISTICS:
        ( A ) LENGTH: 54 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:7:

GGAATTCCGT CCCAGTGATG AAGATCGCAG CGCCCGAGAC TCGGCCGGAT CCGC    54

(2) INFORMATION FOR SEQ ID NO:8:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGAATTCCCT CGGGCGCTGA TCTTCATCAC TGTCCCACTC GGCCGGATCC GC    52

(2) INFORMATION FOR SEQ ID NO:9:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGAATTCCCG AGGAAGGTAG ACGCAATGGC GGCACTCGGC CGGATCCGG    49

(2) INFORMATION FOR SEQ ID NO:10:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGAATTCGCA GCCATTGCGT CTACCAACCT CGGGACTCGG CCGGATCCGG    50

(2) INFORMATION FOR SEQ ID NO:11:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCACCTCTGA CTTGAGCGTC CCAGTGTCAA TACGGCGGAG CCTATGGAGT AACGCC    56

(2) INFORMATION FOR SEQ ID NO:12:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GCAAAAGGCC AGGAACCGAT AAAAGGATGC GTTGCTGGCG TTACTCCATA GGCTCCG　　　　　　57

( 2 ) INFORMATION FOR SEQ ID NO:13:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

CCGGAGCTGA ATGAAGCCAT ACCAAACGAC GAGCGTGACA CCACGATGCC TGCAGCAATG　　60

GCAACAACGT　　　　　　70

( 2 ) INFORMATION FOR SEQ ID NO:14:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GTATTCTGCT GCTCTGTTCC GCCTCGGGTA GACACGTTGT TGCCATTGCT　　50

( 2 ) INFORMATION FOR SEQ ID NO:15:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GGATTCGCCT CCAGATCTGG TCCTCGGGTA GACCCGGAGC TGAATGAAGC　　50

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CATCGTGGTG TCACGCTCGT CGT　　23

( 2 ) INFORMATION FOR SEQ ID NO:17:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

ATACGGGTTA CTGATGATGA ACATGCCCGG TTACTGGAAC GTTGTGAGG　　49

( 2 ) INFORMATION FOR SEQ ID NO:18:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

GAGAATTCGT GGACTGCAGA TCGTTGACGT GATTACCCTC ACAACGTTCC AGTAACC    57

( 2 ) INFORMATION FOR SEQ ID NO:19:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

GAGAATTCGT GGACTGCAGA TGTCTCCAAT CCCCCCTCAC AACGTTCCAG TAACC    55

STRAND DISPLACEMENT AMPLIFICATION USING THERMOPHILIC ENZYMES

FIELD OF THE INVENTION

The invention relates to methods for amplification of nucleic acid target sequences and in particular relates to isothermal methods for amplification of nucleic acid target sequences.

BACKGROUND OF THE INVENTION

In vitro nucleic acid amplification techniques have provided powerful tools for detection and analysis of small amounts of nucleic acids. The extreme sensitivity of such methods has lead to attempts to develop them for diagnosis of infectious and genetic diseases, isolation of genes for analysis, and detection of specific nucleic acids as in forensic medicine. Nucleic acid amplification techniques can be grouped according to the temperature requirements of the procedure. The polymerase chain reaction (PCR; R. K. Saiki, et al. 1985. *Science* 230, 1350–1354), ligase chain reaction (LCR; D. Y. Wu, et al. 1989. *Genomics* 4, 560–569; K. Barringer, et al. 1990. *Gene* 89, 117–122; F. Barany. 1991. *Proc. Natl. Acad. Sci. USA* 88, 189–193), transcription-based amplification (D. Y. Kwoh, et at. 1989. *Proc. Natl. Acad Sci. USA* 86, 1173–1177) and restriction amplification (U.S. Pat. No. 5,102,784) require temperature cycling. In contrast, methods such as Strand Displacement Amplification (SDA; G. T. Walker, et at. 1992. *Proc. Natl. Acad. Sci. USA* 89, 392–396 and G. T. Walker, et al. 1992. *Nuc. Acids. Res.* 20, 1691–1696, and EP 0 497 272, all three disclosures being incorporated herein by reference), self-sustained sequence replication (3SR; J. C. Guatelli, et al. 1990. *Proc. Natl. Acad. Sci. USA* 87, 1874–1878) and the Qβ replicase system (P. M. Lizardi, et al. 1988. *BioTechnology* 6, 1197–1202) are isothermal reactions. In addition, WO 90/10064 and WO 91/03573 describe use of the bacteriophage phi29 replication origin for isothermal replication of nucleic acids. WO 92/05287 describes a method for isothermal production of sequence-specific oligonucleotides in which a modification in one strand allows a cutting agent to selectively cleave the opposite strand. The single stranded complementary oligonucleotide is released, allowing repolymerization of an additional complementary oligonucleotide. Isothermal amplifications are conducted at a constant temperature, in contrast to the cycling between high and low temperatures characteristic of amplification reactions such as the PCR.

The conventional SDA reaction is conducted at a constant temperature between about 37° C. and 42° C. This is because the exo⁻ klenow DNA polymerase and particularly the restriction endonuclease (e.g., HincII) are thermolabile (temperature sensitive). The enzymes which drive the amplification are therefore inactivated as the reaction temperature is increased. However, the ability to conduct isothermal amplification reactions such as SDA at higher temperatures than previously possible could have several advantages. Amplification at elevated temperatures may allow for more stringent annealing between amplification primers and template DNA, thereby improving the specificity of the amplification process. Background reactions could also be reduced as a result of such improved amplification specificity. In SDA, a significant source of background reactions are the short "primer dimers" which are generated when the amplification primers interact with each other. Formation of primer dimers may seriously impair the efficiency of the desired, specific amplification of the target sequence. The formation of such primer dimers is more likely at lower temperatures because the reduced stringency of the reaction allows increased transient hybridization between sequences with limited homology. The ability to conduct SDA at higher temperatures could potentially reduce primer dimer interactions, reduce background and improve the efficiency of specific target amplification. In addition, amplifying at higher temperatures may facilitate strand displacement by the polymerase. Improved strand displacing activity might increase the efficiency of target amplification and result in increased yields of the amplification product. The use of sufficiently heat stable enzymes could also allow all reagents required for the SDA reaction to be added prior to the initial heat denaturation step. Conventional SDA requires that the enzymes be added to the reaction mix after double stranded target sequences have been denatured by heating.

dUTP may be incorporated into amplified target DNA by SDA. This allows amplicons from a prior amplification which may contaminate a subsequent amplification reaction to be rendered unamplifiable by treatment with uracil DNA glycosylase (UDG). The decontamination method itself can be used regardless of the temperature at which the amplicons were generated in the SDA reaction. However, SDA amplification products generated at lower temperatures (i.e., 37° C. to 42° C.) may contain a high level of nonspecific background products. Decontamination of large amounts of background amplicons may seriously impede or inhibit elimination of contaminating target-specific amplicons, thus reducing the efficiency of the decontamination procedure. The ability to perform SDA at higher temperatures, by depressing the amount of non-specific background amplicons generated, could therefore increase the efficiency of the UDG decontamination procedure.

The SDA reaction requires several very specific enzymatic activities in order to successfully amplify a target sequence. Thermophilic polymerases have been reported extensively in the literature. However, as other nucleic acid amplification systems do not require the combination of enzymatic activities of SDA, prior to the present invention little was known about the activities and reaction requirements of thermophilic enzymes as they relate to the biological activities required by SDA. Further, because SDA requires concurrent activity by two different enzymes (restriction endonuclease and polymerase), it was not known prior to the present invention whether or not compatible pairs of such thermophilic enzymes existed. That is, both a thermophilic polymerase and a thermophilic restriction endonuclease are required. These two enzymes must have temperature and reaction condition (e.g., salt) requirements compatible with each other and with SDA in order for both to function efficiently in the same SDA reaction mix. In addition, the polymerase must 1) lack 5'-3' exonuclease activity, either naturally or by inactivation, 2) incorporate the modified nucleotides required by SDA (αthio-dNTPs or other modified dNTPs), 3) displace a downsteam single strand from a double stranded molecule starting at a single stranded nick and preferably 4) incorporate dUTP to allow amplicon decontamination. The polymerase must extend the complementary strand on the template by addition of dNTPs to a free 3'-OH. It is also preferable that the polymerase have a high processivity. That is, the polymerase should be able to add as many nucleotides as possible before dissociating and terminating the extension product. The restriction endonuclease must 1) nick (i.e., cleave a single strand of) its double stranded recognition/cleavage site when the recognition/cleavage site is hemimodified, 2) dissociate from its recognition/cleavage site rapidly enough to allow the polymerase to bind and amplify the target efficiently, and preferably 3) be unaffected by dUTP incorporated into its recognition/cleavage site. In addition, the restriction endonuclease must exhibit these activities under temperature and reaction conditions compatible with the polymerase.

SUMMARY OF THE INVENTION

The present invention provides methods for isothermal Strand Displacement Amplification which can be performed over a broader temperature range (37° C. to 70° C., "thermophilic SDA") than conventional SDA. The preferred temperature range for thermophilic SDA is 50° C. to 70° C. It has been found that certain thermophilic restriction endonucleases are capable of nicking a hemimodified restriction endonuclease recognition/cleavage site as required by SDA and then dissociating from the site. It has further been found that certain thermophilic polymerases are capable of extending from the nick while displacing the downstream strand. These discoveries have made possible development of an SDA method which, by virtue of being performed at higher temperatures than previously possible, has improved specificity and efficiency, reduced nonspecific background amplification, and potentially improved yields of amplification products. In addition, the need to add the enzymes in a separate step after the initial heat denaturation of double stranded targets may be eliminated when enzymes which are stable at the denaturation temperature are used. UDG decontamination of target-specific amplicons in the SDA reaction is also more efficient when the amount of nonspecific background amplicons is reduced.

DETAILED DESCRIPTION OF THE INVENTION

Figure 1:
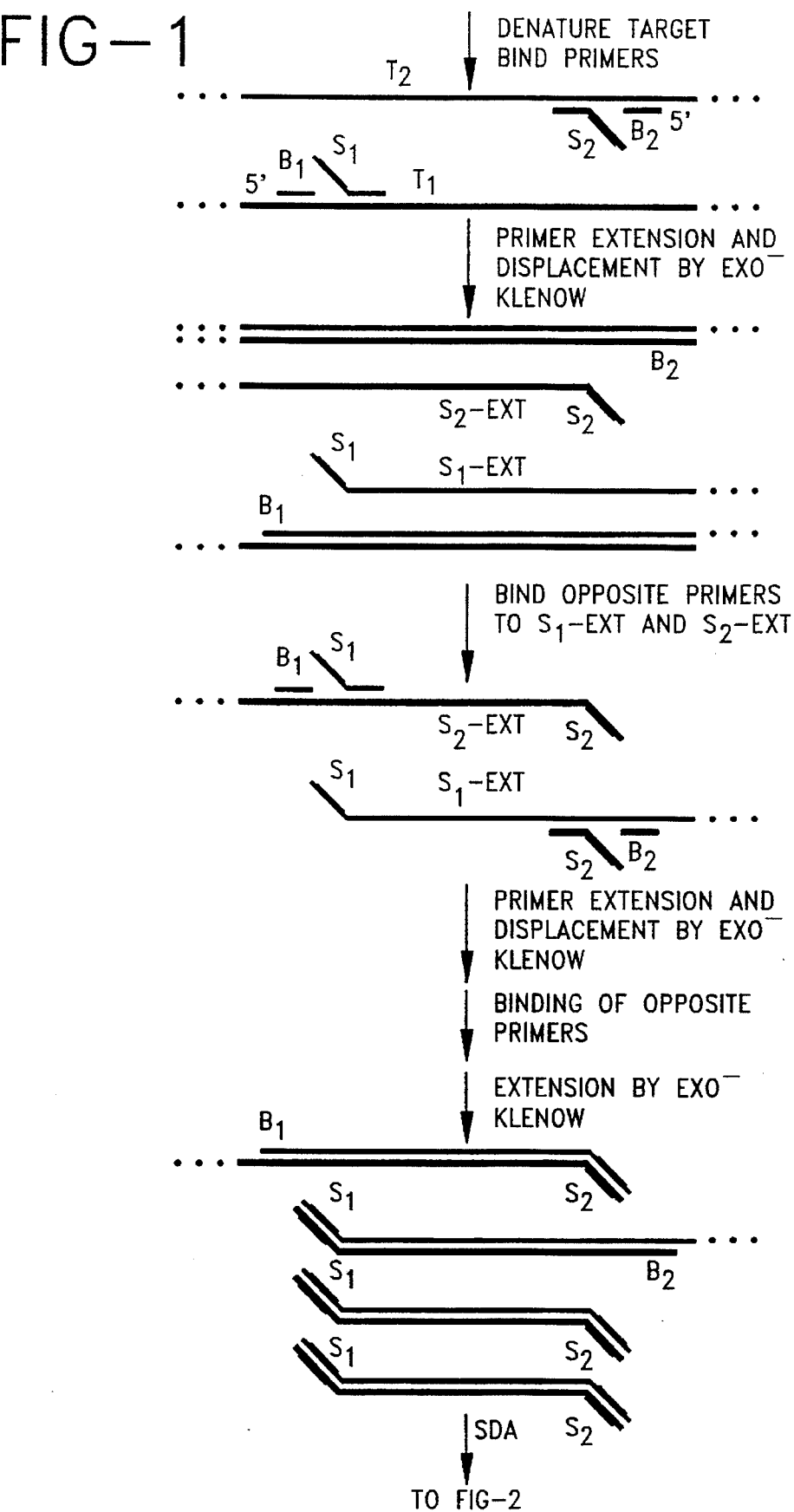
FIG. 1 illustrates the SDA target generation scheme of Walker, et al. (1992. *Nuc. Acids Res.*, supra).
Figure 2:
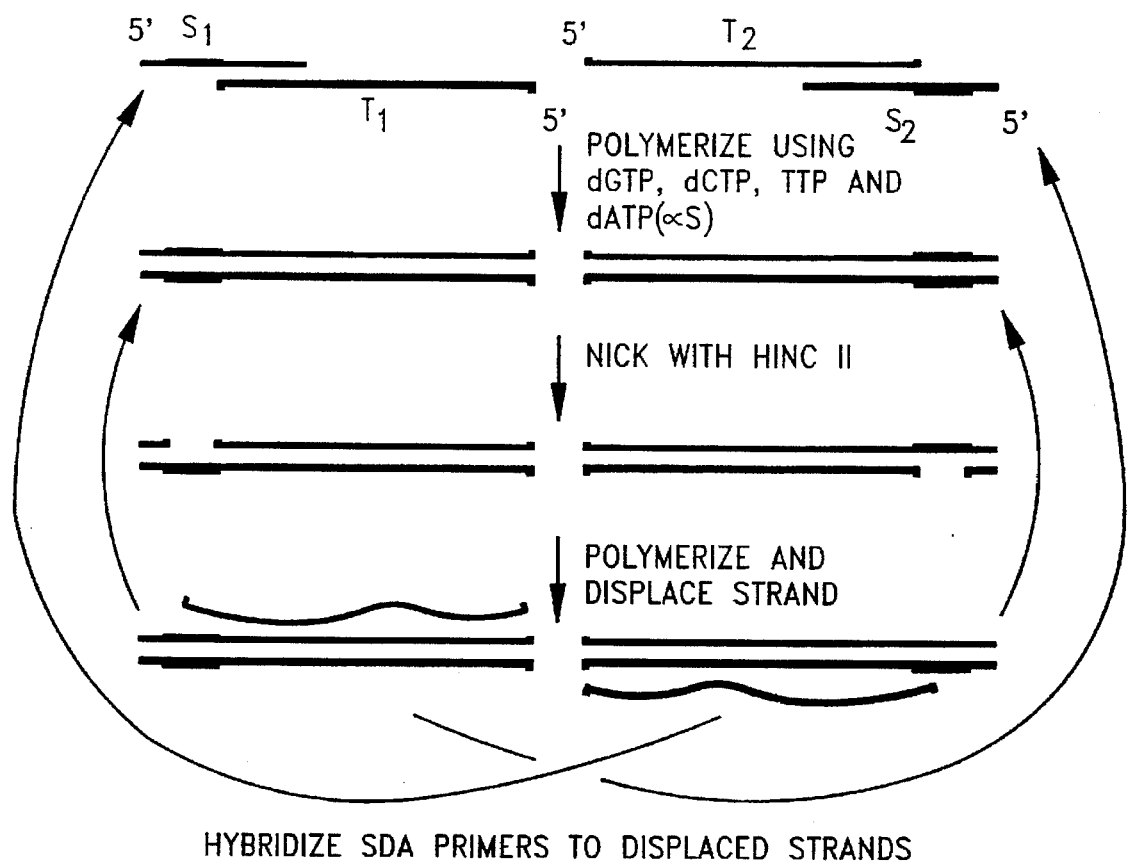
FIG. 2 illustrates the SDA reaction cycle for a double stranded target with two amplification primers (exponential amplification). The portion of FIG. 2 showing the reaction cycle using one of the amplification primers illustrates linear SDA.

As used herein, the following terms and phrases are defined as follows:

An amplification primer is a primer for amplification of a target sequence by primer extension. For SDA, the 3' end of the amplification primer (the target binding sequence) hybridizes at the 3' end of the target sequence. The SDA amplification primer further comprises a recognition/cleavage site for a restriction endonuclease near its 5' end. Additional nucleotides 5' to the recognition/cleavage site may be present to provide for efficient binding of the restriction endonuclease. The recognition/cleavage site is for a restriction endonuclease which will nick one strand of a DNA duplex when the recognition/cleavage site is hemimodified, as described by Walker, et at. (1992. *PNAS*, supra). A hemimodified recognition/cleavage site is a double stranded recognition/cleavage site for a restriction endonuclease in which one strand contains at least one derivatized nucleotide which prevents cutting of one of the two strands by the restriction endonuclease. In most cases, the strand of the hemimodified recognition/cleavage site which initially does not contain derivatized nucleotides is nicked by the restriction endonuclease. After the first SDA cycle, however, half of the recognition/cleavage site of the nicked strand will contain derivatized nucleotides, but this does not prevent subsequent nicking. The preferred hemimodified recognition/cleavage sites for conventional SDA are hemiphosphorothioated recognition/cleavage sites for the restriction endonucleases HincII, HindII, AvaI, NciI and Fnu4HI. The amplification primer also comprises a 3'-OH group which is extendable by DNA polymerase when the target binding sequence of the amplification primer is hybridized to the target sequence. For the majority of the SDA reaction, the amplification primer is responsible for amplification of the target sequence.

Extension products are nucleic acids which comprise a primer (or a portion of a primer) and a newly synthesized strand which is the complement of the target sequence downstream of the primer binding site. Extension products result from hybridization of a primer to a target sequence and extension of the primer by polymerase using the target sequence as a template.

A bumper primer or external primer is a primer which anneals to a target sequence upstream of the amplification primer, such that extension of the bumper primer displaces the downstream amplification primer and its extension product. Extension of bumper primer is one method for displacing the extension products of amplification primers, but heating is also suitable.

Identical sequences will hybridize to the same complementary nucleotide sequence. Substantially identical sequences are sufficiently similar in their nucleotide sequence that they also hybridize to the same partially complementary nucleotide sequence.

The terms target or target sequence refer to nucleic acid sequences to be amplified. These include the original nucleic acid sequence to be amplified, its complementary second strand and either strand of a copy of the original sequence which is produced in the amplification reaction. The target sequence may also be referred to as a template for extension of hybridized amplification primers.

Amplification products, amplified products or amplicons comprise copies of the target sequence and are generated by hybridization and extension of an amplification primer. This term refers to both single stranded and double stranded amplification primer extension products which contain a copy of the original target sequence, including intermediates of the amplification reaction.

Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to the PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (αthio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. (1992, *Nuc. Acids Res.*, supra) and in U.S. Pat. No. 5,270,184 (hereby incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as a targets for binding of the opposite amplification and bumper primer (e.g., the extension product of $S_1$ binds $S_2$ and $B_2$). The next cycle of extension and diplacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with UDG (uracil DNA glycosylase, also known as uracil N-glycosylase or UNG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with Ugi (uracil DNA glycosylase inhibitor, a protein inhibitor of UDG) prior to amplification of the target. Alternatively, UDG may be heat-inactivated. In thermophilic SDA, the higher temperature of the reaction itself ($\geq 50°$ C.) can be used to concurrently inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity is also of great importance, as it is nicking which perpetuates the reaction and allows subsequent rounds of target amplification to initiate.

As little was previously known about the activities of thermophilic polymerases at appropriate temperatures for SDA, a polymerase screening system was developed to identify candidate thermophilic polymerases if any existed. The screening system is an extension assay which tests the ability of the polymerase to displace a downstream strand initiating at a single stranded nick in a double stranded template. The presence of polymerase displacement activity is essential for SDA. However, 5'-3' exonuclease activity, if present in an otherwise suitable thermophilic polymerase, can be inactivated by routine methods known in the art (WO 92/06200). One of the most common methods for selectively inactivating exonuclease activity in a polymerase is to clone the gene for the polymerase, identify the portion of the gene sequence which codes for the protein domain responsible for exonuclease activity, and inactivate it by in vitro mutagenesis. Alternatively, exonuclease activity may be inactivated by treating the polymerase with protease to isolate fragments which exhibit only the desired polymerization and displacing activities. Therefore, a thermophilic polymerase identified in the extension assay which is active at a suitable temperature, initiates extension at a nick and incorporates modified or unconventional dNTPs but has 5'-3' exonuclease activity is not eliminated from consideration for thermophilic SDA.

In the extension assay for polymerases, displacement of the single strand from a double stranded nucleic acid and initiation at a nick is staged by annealing two primers immediately adjacent to each other on an intact sequence complementary to both primers. The primers are labeled at their 5' ends. If a polymerase has strand displacement activity, is able to initiate polymerization at the "nick" formed by the adjacent primers and lacks 5'-3' exonuclease activity, both primers are extended and two extension products will be detected. If the polymerase lacks 5'-3' exonuclease activity but cannot initiate extension at the nick (e.g., it requires a gap) or also lacks displacement activity, only the extension product of the downstream primer will be detected. A polymerase which initiates at a nick but has 5'-3' exonuclease activity will generate only the extension product of the upstream primer.

The following polymerases have been identified as having all of the required characteristics for use in the invention: exo⁻ Vent (New England Biolabs), exo⁻ Deep Vent (New England Biolabs), Bst (BioRad), exo⁻ Pfu (Stratagene), Bca (Panvera), and Sequencing Grade Taq (Promega). Others may be routinely identified using the foregoing extension assay without the exercise of inventive skill, and all such polymerases would be suitable for use in thermophilic SDA. The polymerases Tth (Boehringer), Tfi (Epicentre), REPLI-NASE (DuPont) and REPLITHERM (Epicentre) strand displace from a nick, but also have 5'-3' exonuclease activity. These polymerases are useful in the methods of the invention after removal of the exonuclease activity, e.g., by genetic engineering. Most of the thermophilic polymerases identified so far have optimal activity at 65° C.–75° C. and markedly reduced activity at 50° C.–60° C. However, as the thermostability of thermophilic restriction endonucleases is generally limited to less than 65° C., thermophilic polymerases with optimal activity at lower temperatures (e.g., Bst and Bca) are more compatible with thermophilic restriction endonucleases in the reaction and are therefore preferred.

The restriction endonuclease must dissociate from the recognition/cleavage site sufficiently quickly to allow efficient amplification of the target sequence, allowing the polymerase to bind promptly at the nick and initiate extension. Restriction endonucleases suitable for SDA also must cleave only the primer strand of a double stranded hemimodified recognition/cleavage site for the restriction endonuclease ("nicking"). Because restriction enzymes generally produce double strand breaks, cleavage of one of the two strands in the duplex of the cleavage site must be selectively inhibited. This is usually accomplished by introducing nucleotide analogs (e.g., deoxynucleoside phosphorothioates) into one strand of the DNA during synthesis so that the modified strand is no longer susceptible to cleavage. In some cases, introduction of nucleotide analogs may result in the unmodified strand being no longer susceptible to cleavage. In cases where the unmodified strand is protected from cleavage, nucleotide analogs may be incorporated during synthesis of the primer to cause nicking, thus eliminating the need to add nucleotide analogs to the amplification reaction and the requirement that the polymerase be capable of incorporating such nucleotide analogs.

Nucleotide analog substitutions do not protect the primer strand from all restriction endonucleases, however. A means for assessing the nicking characteristics of restriction endonucleases was therefore required in order to identify suitable enzymes among the many available thermophilic restriction endonucleases, if such enzymes existed. Therefore, a screening system for identifying thermophilic restriction endonucleases with the desired properties was devised based on the ability of a modified deoxynucleotide incorporated into one strand of the double stranded restriction endonuclease recognition/cleavage site to protect one of the two strands from cleavage by the endonuclease. This is referred to as the analog-induced nicking assay or the strand protection assay.

In the assay, a single stranded template and a complementary primer are synthesized. The template and the primer are then labeled, preferably with a radiolabel. The primer and template are hybridized and modified dNTPs are incorporated by extension of the primer, producing a fully double stranded molecule containing a hemimodified restriction endonuclease recognition/cleavage site. This product is treated with the restriction endonuclease under appropriate conditions for cleavage. Electrophoretic analysis of the reaction products under denaturing conditions is used to determine, by the size of the fragments generated, whether or not the recognition/cleavage site was nicked, cleaved or uncut. The size of the fragments on electrophoresis was also used to determine which of the two strands of the recognition/cleavage site (i.e., modified or unmodified) was protected from cleavage.

Thermophilic SDA is performed essentially as the conventional SDA described by Walker, et al. (1992. *PNAS* and *Nuc. Acids Res.*, supra), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in thermophilic SDA are BsrI, BstNI, BsmAI, BslI and BsoBI (New England BioLabs), and BstOI (Promega). The preferred thermophilic polymerases are Bca and Bst.

To develop an optimized SDA system capable of high amplification factors (e.g., $10^8$–$10^9$), evaluation and optimization of the buffer systems is recommended. This is also the case when evaluating a new restriction enzyme/polymerase pairing for use in thermophilic SDA. The manufacturer provides a recommended buffer for the restriction endonuclease which is usually a Tris buffer with 10 mM $MgCl_2$. It may also contain 50–150 mM either NaCl and/or KCl. These conditions are not necessarily optimized for thermophilic SDA but, instead, are intended to provide 100% double strand cleavage of nucleic acids at the recommended temperature. In SDA, the restriction endonuclease recognizes its double-stranded site, however, the substitution of the derivatized dNTP induces the endonuclease to nick the primer strand rather than cleave both strands. The manufacturer-recommended buffer may therefore not be the optimum buffer for expression of this modified restriction endonuclease behavior. In addition, the restriction endonuclease must function in concert with a polymerase in SDA. The buffer system must therefore support both nicking by the restriction enzyme and extension/displacement by the polymerase in order for the SDA reaction to occur.

When evaluating a buffer system for use with a new SDA restriction endonuclease, it is generally useful to begin buffer optimization by evaluating the recommended buffer for the restriction enzyme. Using a subtractive method one can determine which components are essential for the nicking action of the endonuclease. Combining this information with buffer conditions which are known to enhance polymerase activity in SDA, a prototype buffering system can be developed. As discussed above, an important aspect of buffer optimization is the interactive nature of the components. For this reason, it is desirable to test various concentrations of different components rather than keeping one component constant and varying the others one at a time. For example, if various MgCl$_2$ concentrations are examined while keeping the KPO$_4$ constant, the result is the best MgCl$_2$ concentration at that particular concentration of KPO$_4$. But if various combinations MgCl$_2$ and KPO$_4$ concentration are examined the result is the combined concentrations of MgCl$_2$ and KPO$_4$ which provide the best result. Therefore, each of the buffer components should be examined simultaneously to insure that the concerted effects of the components provides optimum amplification. This method is described in detail in *Experimental Design in Biotechnology* by Dr. Perry Haaland (Marcell Dekker, NY, 1989).

The methods for buffer optimization for conventional SDA are useful for thermophilic SDA. The buffer for conventional SDA (employing HincII/exo-Klenow) was developed as follows: SDA was performed using each of the commercially available buffers for restriction endonucleases. These buffers contained 20–50 mM Tris pH 7.4–8, 50–150 mM NaCl and/or KCl (or the acetate salts) and 5–12 mM MgCl$_2$. The buffer that best supported SDA for HincII was REACT 6 from GIBCO-BRL, although the manufacturer recommended REACT 4 for use with HincII for double strand cleavage (20 mM Tris, pH 7.4, 5 mM MgCl$_2$ and 50 mM KCl). REACT 6 buffer contains 50 mM Tris pH 7.4, 6 mM MgCl$_2$, 50 mM NaCl and 50 mM KCl. Further experiments were performed in which it was determined that MgCl$_2$ and K$^+$ were the most important buffer components. A KPO$_4$ buffer was therefore substituted for Tris as the K$^+$ source. This buffer supported both restriction endonuclease activity and polymerase activity, resulting in high levels of amplification in the conventional SDA reaction. Using KPO$_4$ buffers with restriction endonucleases is not typical, but proved to be appropriate for the restriction endonuclease/polymerase combination in SDA upon analysis of the buffer components. More common buffers (i.e Tris) have been examined in a similar fashion but do not further enhance amplification.

Similar optimization methods may be applied to determine an appropriate buffer for any restriction endonuclease/polymerase combination for thermophilic SDA, requiring only routine testing without the exercise of inventive skill. In many cases the KPO$_4$/MgCl$_2$ buffer typically employed in conventional SDA is suitable for thermophilic SDA, either as described or with some routine modification of the concentrations of these components (see Example 5).

EXAMPLE 1

Extension Assay Screening of Polymerases

Using plasmid pBR322 as a target, two primers were synthesized which annealed immediately adjacent to each other on the plasmid. Primer PBR1 was the upstream primer and corresponded to bases 3661–3690 in pBR322. Primer PBR2 hybridized downstream of PBR1 and corresponded to bases 3691–3720. These 30-mer oligonucleotides were synthesized using an Applied Biosystems DNA synthesizer, Model 380, and purified by electroelution from a denaturing acrylamide gel. The primers were labeled separately in kinase reactions using 10 µM primer, 50 mM Tris, pH 7.5, 10 mM MgCl$_2$, 70 µCi $^{32}$P-ATP and 10 units polynucleotide kinase in a reaction volume of 10 µL for 30 minutes at 37° C. The labeled primers were combined with 200 ng of PstI/HincII digested pBR322 at a final concentration of 0.2 µM (each primer). The target pBR322 DNA was denatured at 98° C. for 3 minutes in a buffer containing 25 mM KPO$_4$ pH 7.4, 2–8 mM MgCl$_2$ and 0.2–1 mM dNTPs. The mixture was then cooled to the selected reaction temperature (50°–70° C.) for 2 minutes. One unit of the polymerase was added and the reaction was allowed to proceed for 10 minutes. The reactions were stopped by addition of an equal volume of 95% formamide/50 mM EDTA/bromophenol blue dye. Twenty-five µL of the reaction were electrophoresed over a 6% denaturing gel and the gel was exposed to autoradiographic film (Kodak, XAR5).

The above reaction conditions were used in the assay to test the activities of the polymerases at 50° C., 60° C. and 70° C. In each instance, the polymerase was tested in the presence of either all conventional deoxynucleotides (dNTPs) or in the presence of the conventional dNTPs and one thio-substituted deoxynucleotide (αthio dCTP, "dCTPαS mix"). The polymerases tested and the reaction conditions are shown in the following Table:

| Rxn# | Temp (°C.) | dNTP or dC$_S$TP mix | MgCl$_2$ | Polymerase (1 unit) |
|---|---|---|---|---|
| 1 | 50 | 1 mM dNTP | 8 mM | Bst |
| 2 | 50 | 1 mM dCTPαS mix | 8 mM | Bst |
| 3 | 50 | 0.2 mM dNTP | 4 mM | Bca |
| 4 | 50 | 0.2 mM dCTPαS mix | 4 mM | Bca |
| 5 | 50 | 1 mM dNTP | 5.2 mM | exo-Deep Vent |
| 6 | 50 | 1 mM dCTPαS mix | 5.2 mM | exo-Deep Vent |
| 7 | 50 | 0.2 mM dNTP | 2 mM | exo-Vent |
| 8 | 50 | 0.2 mM dCTPαS mix | 2 mM | exo-Vent |
| 9 | 50 | 0.2 mM dNTP | 2 mM | exo-Pfu |
| 10 | 50 | 0.2 mM dCTPαS mix | 2 mM | exo-Pfu |
| 11 | 60 | 1 mM dNTP | 8 mM | Bst |
| 12 | 60 | 1 mM dCTPαS mix | 8 mM | Bst |
| 13 | 60 | 0.2 mM dNTP | 4 mM | Bca |
| 14 | 60 | 0.2 mM dCTPαS mix | 4 mM | Bca |
| 15 | 60 | 1 mM dNTP | 5.2 mM | exo-Deep Vent |
| 16 | 60 | 1 mM dCTPαS mix | 5.2 mM | exo-Deep Vent |
| 17 | 60 | 0.2 mM dNTP | 2 mM | exo-Vent |
| 18 | 60 | 0.2 mM dCTPαS mix | 2 mM | exo-Vent |
| 19 | 60 | 0.2 mM dNTP | 2 mM | exo-Pfu |
| 20 | 60 | 0.2 mM dCTPαS mix | 2 mM | exo-Pfu |
| 21 | 70 | 1 mM dNTP | 8 mM | Bst |
| 22 | 70 | 1 mM dCTPαS mix | 8 mM | Bst |
| 23 | 70 | 0.2 mM dNTP | 4 mM | Bca |
| 24 | 70 | 0.2 mM dCTPαS mix | 4 mM | Bca |
| 25 | 70 | 1 mM dNTP | 5.2 mM | exo-Deep Vent |
| 26 | 70 | 1 mM dCTPαS mix | 5.2 mM | exo-Deep Vent |
| 27 | 70 | 0.2 mM dNTP | 2 mM | exo-Vent |
| 28 | 70 | 0.2 mM dCTPαS mix | 2 mM | exo-Vent |
| 29 | 70 | 0.2 mM dNTP | 2 mM | exo-Pfu |
| 30 | 70 | 0.2 mM dCTPαS mix | 2 mM | exo-Pfu |

Polymerases which were able to extend both primers with displacement of the downstream, newly synthesized strand generated two bands on the autoradiograph. The larger band represents extension of PBR1 to the HincII site of the digested target plasmid and is 244 nucleotides in length. The smaller band is the extension product of PBR2 extended to the HincII site and is 214 nucleotides in length. When only one extension product was generated, only one band was detected on the autoradiograph. When the only band was the smaller of the two, only the downstream primer (PBR2) had been extended. Such polymerases would not be suitable for SDA, either because they are not capable of extending the upstream primer by initiating extension at the nick or because they are not capable of displacing the strand downstream from the nick. When only the larger band was detected, polymerization had initiated at the nick, but the polymerase also exhibited 5'-3' exonuclease activity.

The activity profiles of the polymerases identified in the extension assay which are useful for thermophilic SDA are summarized in the following table:

| POLYMERASE | STRAND DISPLACE | 5'-3'-EXO | OPTIMUM TEMP | SOURCE |
|---|---|---|---|---|
| Bst (*B. stearothermophilus*) | Yes | No | 65° C. | BioRad & MBR |
| Bca (*B. caldotenax*) | Yes | No | 65° C. | Panvera (Takara) |
| exo-Vent (*Thermococcus litoralis*) | Yes | No | 72° C. | NEB |
| exo-Deep Vent (*Pyrococcus sp.* GB-D) | Yes | No | 72° C. | NEB |
| exo-Pfu | Yes | No | 72° C. | Stratagene |
| Tth (*Thermus thermophilus* HB-8) | Yes | Yes | 72° C. | Boehringer Mannheim & Epicentre |
| Tfl (*Thermos flavus*) | Yes | Yes | 72° C. | Epicentre |
| Replinase | Yes | Yes | 72° C. | DuPont |
| Replitherm | Yes | Yes | 72° C. | Epicentre |
| Taq (*Thermus aquaticus*) | Yes | Yes | 72° C. | Perkin-Elmer Cetus, USB & Boehringer-Mannheim |
| Sequencing Grade Taq (*Thermus aquaticus*) | Yes | No | 72° C. | Promega |

Bst polymerase (BioRad) and Bca polymerase (Panvera, Takara, also known as Ladderman polymerase) produced both extension products in the assay. Of the polymerases tested in this example, only only these two exhibited all of the required attributes (initiation at the nick, strand displacement and incorporation of thio-substituted deoxynucleotides) over the entire temperature range 50° C. to 70° C. The Bca and Bst polymerases are therefore useful in thermophilic SDA reactions over the entire range of 50° C. to 70° C. under normal buffering conditions. A second group of polymerases (Exo⁻ Vent, exo⁻ Deep Vent and exo⁻ Pfu) produced the PBR2 extension product across the temperature range, but failed to produce significant amounts of the PBR1 extension product below 70° C. Using these three polymerases, none of the 244 nucleotide PBR1 extension product was detected at 50° C. and only a small amount was detectable at 60° C. However, a significant amount of each of the two extension products was produced at 70° C. These results indicate that displacing activity and/or initiation at a nick are temperature dependent activities for Exo⁻ Vent, exo⁻ Deep Vent and exo⁻ Pfu. They were, however, capable of incorporating thio-substituted deoxynucleotides and had all of the other activities required for SDA. The polymerases in this second group are useful in thermophilic SDA in conjunction with a restriction endonuclease which is functional at about 70° C. or higher, preferably with a restriction endonuclease which has a temperature optimum at about 70° C. Alternatively, their displacing activity can be enhanced at lower temperatures by addition of a solvent, such as about 15% glycerol or about 15% DMSO.

Only the PBR1 extension product was seen when Sequencing Grade Taq, Tth, Tfl, REPLINASE and REPLITHERM polymerases were tested in the assay. These results indicate that these polymerases are capable of initiating polymerization at a nick, but they have 5'-3' exonuclease activity. With selective elimination of the 5'-3' exonuclease activity using methods known in the art, this group of polymerases is also useful in thermophilic SDA.

EXAMPLE 2

Strand Protection Assay for Screening of Restriction Endonucleases

Double stranded oligonucleotides containing hemimodified recognition/cleavage sites for restriction endonucleases were constructed. The double stranded oligonucleotides were constructed by first synthesizing a common primer 16 nucleotides in length (SEQ ID NO:1 or SEQ ID NO:2) and various template strands 44–57 nucleotides in length. Each template strand contained multiple recognition/cleavage sites in tandem, usually with filler sequences in between each site. Cleavage sites were positioned on the oligonucleotide such that nicking or cleavage of each site would result in a fragment which would be distinguishable by size on a gel. In some cases where the endonuclease exhibited degenerate recognition/cleavage sites, several of these were tested. The templates synthesized were as follows:

CDAva1S1 (SEQ ID NO:3): 5'-TACAATAGTCCC-AATCTACCCGAGCTTACACGGAGGCATCAAGTG-3'

CDAva2S1 (SEQ ID NO:4): 5'-TACAATAGTCCC-AATCTACTCGGGCTTACACGGAGGCATCAAGTG-3'

TP-1 (SEQ ID NO:5): 5'-CCGGAATTCGAA-TGCCAAAAGACTGGGTCTCCAGGAACCAACTC-GGCCGGATCCGC-3'

TP-1C (SEQ ID NO:6): 5'-CCGGAATT-CTGGTTCCTGGAGACCCAGTCTTTTGGCATTCA-CTCGGCCGGATCCGC-3'

TP-3 (SEQ ID NO:7): 5'-GGAATTCCG-TCCCAGTGATGAAGATCGCAGCGCCCGAGACTC-GGCCGGATCCGC-3'

TP-3C (SEQ ID NO:8): 5'-GGAATTCCCTC-GGGCGCTGATCTTCATCACTGTCCCACTCGGCC-GGATCCGC-3'

TP-4 (SEQ ID NO:9): 5'-GGAATTCCC-GAGGAAGGTAGACGCAATGGCGGCACTCGGCC-GGATCCGG-3'

TP-4C (SEQ ID NO:10): 5'-GGAATTCG-CAGCCATTGCGTCTACCAACCTCGGGACTCGGC-CGGATCCGG-3'

SSP-BSMA (SEQ ID NO:19) 5'-GAGAATTC-GTGGACTGCAGATGTCTCCAATCCCCCCTCACA-ACGTTCCAGTAACC-3'

SEQ ID NO:1 primes SEQ ID NO:5–10 and SEQ ID NO:2 primes SEQ ID NO:2–4. These templates contain recognition/cleavage sites for the following restriction endonucleases: AccI, AspI, BsaI, BsaBI, BsiYI, BsII, BsmI (two degenerate sites), BsmAI, BsmFI, BsmHI, BspWI, BsoBI (four degenerate sites), BsoFI, BsrI (two degenerate sites), BsrBRI, BsrDI (two degenerate sites), Bst71I, BstNI (two degenerate sites), BstOI, BstXI, DpnI, HaeII, MamI, MboII, MvaI, MwoI, SfiI, and Tth111I.

The primers and templates were purified by gel electrophoresis after synthesis and electroeluted from gel slices using standard methods. They were then 5' end-labeled using T4 polynucleotide kinase and γ-[$^{32}$P]-adenosine triphosphate for later autoradiographic detection. A typical kinase reaction contained 2 μL of 10X kinase buffer (New England Biolabs), 10 μL of γ-[$^{32}$P]-ATP (3000 curies/mmol, NEN-DuPont), primer or template to give a final concentration of 1 μM, 20 units T4 polynucleotide kinase (New England Biolabs), and water to make a total reaction volume of 20 μL. Kinase reactions were performed at 37° C. for 30 min., then terminated by heating in boiling water for 5 min. The primer was then hybridized to each of the templates and extended using polymerase and various phosphorothioate-substituted nucleotides, producing a double-stranded oligonucleotide in which the recognition/cleavage sites were hemimodified. Derivatized dNTPs were incorporated into one or the other of the two strands of the recognition/cleavage sites in different experiments to test the effect on nicking activity. The radiolabeled primer and template were then annealed by mixing 2 μL of each, 1 μL of REACT-1 buffer (Life Technologies), and 11.5 μL of deionized, distilled water in a closed 0.5 mL polypropylene microfuge tube. This mixture was heated for 3 min. in a boiling water bath, then allowed to cool slowly to 37° C. by removing the water bath from the heat source. The tubes were then transferred to a 37° C. incubator and the hybridized primers were extended on the template by adding 1 μL of the appropriate mix of deoxynucleoside triphosphates (dNTPs) including at least one thio-dNTP, 2 μL of 10 mM dithiothreitol (DTT), and 0.5 μL of a 10 unit/μL solution of exonuclease deficient Klenow polymerase (U.S. Biochemicals). The final concentration of each dNTP in the extension reaction was 250 μM. Primer extension reactions were allowed to proceed for 20 min. and were then terminated by heating at 75° C. for 10 min.

After extension, aliquots were diluted 10-fold into the appropriate buffer for restriction endonuclease activity as recommended by the supplier of the restriction endonuclease. The final concentration of DNA molecules in the assay was 10 nM. Strand protection assays were initiated by adding 5–10 units of the appropriate restriction endonuclease to each reaction mix. The reactions were incubated at the temperature recommended by the supplier of the restriction endonuclease. Samples were removed at regular intervals and added to an equal volume of formamide sequencing reaction stop solution (U.S. Biochemicals) to quench the reaction. Quenched samples were stored on ice until all were collected. The samples were then heated in a boiling water bath for 3 min. and loaded onto 8% polyacrylamide, 7M urea DNA sequencing gels in Tris-borate buffer (Gibco-BRL). Electrophoresis was performed at a constant power level of 57W for 1 hour. Radiolabeled DNA bands were visualized by autoradiography using Fuji RX grade x-ray film.

Of the thermophilic restriction endonucleases tested, eleven which completely or nearly completely nicked the hemimodified recognition/cleavage site were identified in this study: They are listed in the following table. In some cases, only one of the degenerate sites for the restriction endonuclease was nicked when hemimodified in the strand protection assay. The position of the recognition/cleavage site in the templates is indicated by nucleotide position along with the results of the various phosphorothioate substitutions. If incorporation of a dNTPαS gave complete or nearly complete protection of the derivatized strand (i.e., the unmodified strand was nicked), the nucleotide substitution is listed. "None" indicates that no thionucleotide substitutions were found which resulted in nicking.

| ENZYME | TEMPLATE | RECOGNITION SITE† | PROTECTION WITH dNTPαS |
|---|---|---|---|
| AccI | SEQ ID NO:9 | 17–22 | C |
| BsII | SEQ ID NO:9 | 7–17 | C |
| BsmI | SEQ ID NO:5 | 10–15 | C - unmodified strand protected |
|  | SEQ ID NO:6 | 35–40 | A - modified strand protected |
| BsmAI | SEQ ID NO:5 | 27–31 | G + T |
|  | SEQ ID NO:19 | 22–31 | G |
| BsoBI | SEQ ID NO:7 | 33–38 | None |
|  | SEQ ID NO:10 | 29–34 | C |
|  | SEQ ID NO:3 | 19–24 | T |
|  | SEQ ID NO:4 | 19–24 | C |
| BsrI | SEQ ID NO:5 | 22–26 | None |
|  | SEQ ID NO:7 | 12–16 | A |
| BsrDI | SEQ ID NO:9 | 23–28 | None |
|  | SEQ ID NO:10 | 13–18 | T |
| BstNI | SEQ ID NO:5 | 31–35 | None |
|  | SEQ ID NO:6 | 15–19 | A + C |
| BstOI | SEQ ID NO:5 | 31–35 | None |
|  | SEQ ID NO:6 | 15–19 | A + C |
| BstXI | SEQ ID NO:5 | 15–27 | T |
| MwoI | SED ID NO:9 | 23–33 | G + T |

†Recognition sites are given in nucleotides from the 5' end of the template strand.

It is interesting to note that the recognition site in SEQ D NO:5 at position 10–15 for BsmI exhibits protection of the unmodified strand, i.e., the modified strand is nicked. This suggests the possibility of using this recognition site in conjunction with thio-derivatized primers in thermophilic SDA in place of the conventional unmodified primers. In such a system, nicking and displacing would proceed in the absence of derivatized dNTPs, eliminating the need for the polymerase to be capable of incorporating derivatized dNTPs.

These candidate restriction endonucleases were further tested for their thermal stability in the 50° C. to 65° C. range. Only AccI had unsatisfactory stability in this temperature range and could not stabilized by addition of common stabilizers such as double-stranded DNA and BSA. The remaining nine restriction endonucleases were tested in a linear SDA reaction as in Example 3. All resulted in amplification product except MwoI. It is possible that this enzyme dissociates too slowly from its nicked recognition/cleavage site or is not able to nick the site again (i.e., to initiate subsequent amplification cycles) after the first extension step incorporates thiolated nucleotides into both strands of the recognition/cleavage site. Alternatively, MwoI nicking activity may be incompatible with the buffer system and may therefore be optimizable as described above, making MwoI also useful in thermophilic SDA.

Linear SDA as in Example 3 was performed using BsoBI, BsrI, BstNI, BsmAI and BsII with substitution of dUTP for TTP. This was to confirm the compatibility of these restriction endonucleases with UDG decontamination methods. BsoBI, BstNI and BsmAI were not negatively affected by dU in their recognition/cleavage sites, but the efficiency of linear SDA was reduced for BsrI and BsII under these conditions. Because the Bst and Bca polymerases appear to be unaffected by dUTP substitution, reduced nicking activity for BsrI and BsII is probably due to the incorporation of dU into the recognition/cleavage site of the enzyme. As the cleavage site for BsII occurs in a degenerate sequence, it is believed the site can be altered to overcome the effect of dU on the nicking activity of this enzyme.

Several thermophilic restriction endonucleases were identified which have partial or low nicking activity under the initial screening conditions of the strand protection assay (e.g., Tth111I, BsiYI and BsoFI). Nicking activity of these endonucleases may be optimized by optimizing the the reaction conditions (e.g., by optimizing the buffer or adjusting the reaction temperature), rendering them more useful for thermophilic SDA. In addition, as it is known that sequences flanking a restriction endonuclease recognition/ cleavage site may affect endonuclease activity, altering the flanking sequences of the templates may also improve nicking activity for endonucleases which nicked only partially or promote nicking activity in endonucleases which did not nick under the conditions of this example.

EXAMPLE 3

Linear Thermophilic SDA

The polymerase Bst and the restriction endonuclease BsrI were tested in a linear SDA reaction performed at 60° C. Successful amplification of the target sequence indicates not only that both the polymerase and the restriction endonuclease are functioning under the conditions of the thermophilic SDA reaction, but also that SDA "turnover" is occurring, i.e., the restriction endonuclease dissociates after nicking the hemimodified recognition/cleavage site so as to allow initiation of polymerization, with repetition of the cycle following polymerization.

Two DNA oligomers having the following nucleotide sequences were synthesized:

CCACCTCTGACTTGAGCGTCCCAGTGT-CAATACGGCGGAGCCTATGGAGTAACGCC (SEQ ID NO:11)

GCAAAAGGCCAGGAACCGATAAAAGGAT-GCGTTGCTGGCGTTACTCCATAGGCTCCG (SEQ ID NO:12)

These oligomers hybridize to each other with a 21 base pair overlap and protruding single-stranded 5' ends. The BsrI recognition/cleavage site is indicated in SEQ ID NO:11 by underlined italics.

The oligomers were annealed by incubating at 100° C. for 3 minutes, followed by slow cooling to 60° C. They were then extended to form a completely double-stranded fragment using Bst polymerase, three conventional deoxynucleotides (dCTP, dTTP and dGTP, one of which carded an $\alpha$-$^{32}$P label) and 2'-deoxyadenosine 5'-O-(1-thiotriphosphate) (dATP$\alpha$S). This duplex was 92 nucleotides in length. BsrI endonuclease was then added to start the amplification reaction (time=0). BsrI nicks the unmodified strand of the recognition/cleavage site between the two C's when the complementary strand contains the modified adenosine. The polymerase then initiates at the nick and polymerizes in the 5'-3' direction, displacing a single stranded oligomer 70 nucleotides in length. After the first cycle of polymerization, the endonuclease recognition/cleavage site is regenerated but the strand of the recognition/cleavage site which was previously unmodified is partially substituted with dA$\alpha$S 3' to the nick. This does not interfere with SDA, however. Repetitive cycles of nicking and polymerizing generate multiple copies of the 70 nucleotide extension product from each duplex initially present in the reaction.

SDA reactions were performed at 60° C. in 20 µL of a buffer comprising 25 mM K$_i$PO$_4$ pH 7.6; 6 mM MgCl$_2$; 50 mM KCl, 0.5 mM dCTP, TTP, dGTP and dATP$\alpha$S; 100 µCi [$\alpha$-$^{32}$P] dCTP (3000 Ci/mmol); 50 nM each oligomer; 50 units BsrI endonuclease and 2 units Bst polymerase. Aliquots (5 µL) were removed from the reactions after 5, 10 and 20 minutes. Labeled products were separated by electrophoresis on a denaturing polyacrylamide gel and visualized by autoradiography. A first series of SDA reactions contained the complete list of reagents given above. In a second series of SDA reactions BsrI was omitted. In a third series of SDA reactions Bst polymerase was inactivated by heating (100° C., 5 min.) after formation of the duplex and prior to addition of the restriction endonuclease.

The expected 70 nucleotide extension product was detected in the first reaction series at the first time point (5 minutes) and thereafter. A band corresponding to the intact complementary strand, 92 nucleotides long, could also be seen. The second series of reactions showed only the 92 nucleotide reaction product, as without the nicking activity of BsrI no 70 nucleotide extension products could be generated. The third series of reactions showed only nicking of the duplex, evidenced by a faint band 70 nucleotides in length and a faint band 92 nucleotides in length, both resulting from the unamplified duplexes initially present in the reaction. The turnover rate of the SDA cycle in this experiment was estimated from the film density to be approximately 1 min$^{-1}$.

EXAMPLE 4

Exponential Thermophilic SDA

BsoBI (isolated by New England BioLabs from a Bacillus species) and Bca polymerase (PanVera Corporation, cloned from *Bacillus caldotenax*) were used to demonstrate exponential amplification of a target sequence by thermophilic SDA. Complementary oligomers were synthesized to serve as the two single strands of a double stranded target sequence (SEQ ID NO:13). Five µL, containing various concentrations of this target sequence, was added to each of the reaction mixtures. Some reactions received no target sequence. Amplification primers were also synthesized. Primer XBsoB1-1 (SEQ ID NO:14) contained a BsoBI restriction endonuclease recognition/cleavage site in single stranded form, as did primer XBsoB1-2 (SEQ ID NO:15).

Primer XBsoB1-1 hybridizes to one strand of the target sequence to form a 17 base pair overlap with protruding single stranded 5' ends. Extension of the recessed double stranded 3' ends by the polymerase renders a completely double-stranded fragment 103 nucleotides long containing a double stranded hemimodified BsoBI recognition/cleavage site. Similarly, primer XBsoB1-2 hybridizes to the opposite strand of the target sequence to form a 17 base pair double stranded overlap with protruding single stranded 5' ends. This structure is also filled in by polymerase to generate a double stranded 103-mer containing a double stranded hemimodified BsoBI recognition/cleavage site.

The reaction mixtures, minus Bca and BsoBI, were heated for 3 minutes to denature the target DNA, then cooled to the reaction temperature of 60° C. After equilibration for 3 minutes, 4 units of Bca polymerase and 16 units of BsoBI were added in a total volume of 5 µL. The final concentration of reagents in the reaction mixtures (final volume 50 µL) was 25 mM K$_{i4}$ pH 7.6; 1.375 mM each dCTP$\alpha$S, dATP, dGTP and dTTP; 100 µg/ml acetylated bovine seam albumin; 6.5 mM MgCl$_2$; 0.05 µM XBsoB1-1; 0.05 µM XBsoB1-2; 16 units BsoBI, 4 units Bca, ± the target sequence. The amplification reactions were allowed to proceed for 1 hour, then stopped by placing the tubes in a boiling water bath for 5 minutes.

Amplification products were detected as follows. A 10 µL aliquot of each reaction was removed and a $^{32}$P-labeled primer (SEQ ID NO:16) was added. After hybridizing the primer to any amplification products present, the primer was extended to diagnostic length by addition of polymerase as described by Walker, et at. 1992. *Nuc. Acids Res.*, supra. Ten µL of a denaturing loading solution were added to the aliquot, which was then heated. Ten µL were electrophoresed on denaturing polyacrylamide gels for analysis.

The predicted lengths of detectable oligonucleotides in this experiment were 1) 58 nucleotides, produced by extension of the primer on the nicked, displaced amplification product, and 2) 81 nucleotides, produced by extension of the primer on the intact, full length target. The method was sufficiently sensitive that amplification product was detected when as few as 150 molecules of target sequence were added to the amplification reaction, even though reaction conditions were not optimized.

EXAMPLE 5

Comparison of Conventional and Thermophilic SDA

Thermophilic linear SDA using BsoBI as the restriction endonuclease was compared to conventional linear SDA using HincII. The amplification reactions were performed under the following conditions:

HincII (Reaction Condition A)
  45 mM $K_{i4}$, pH 7.6
  10% DMSO
  0.25 mM each dATPαS, dCTP, dGTP, dTTP
  100 µg/mL acetylated bovine serum albumin
  6 mM $MgCl_2$
  50 nM primer/target complex (SEQ ID NO:17 and SEQ ID NO:18)
  150 units HincII
  10 USB units exo⁻ klenow polymerase
  0.01 mCi α-$^{32}$P-dCTP BsoBI (Reaction Condition B)
  25 mM $K_{i4}$, pH 8.3
  0.25 mM each dCTPαS, dATP, dGTP, dTTP
  100 µg/mL acetylated bovine serum albumin
  15 mM $MgCl_2$
  50 nM primer/target complex (SEQ ID NO:15 and SEQ ID NO:13 complementary strand)
  16 units BsoBI
  4 units Bca polymerase
  0.01 mCi α-$^{32}$P-dATP BsoBI (Reaction Condition C)
  25 mM $K_{i4}$, pH 8.3
  0.25 mM each dCTPαS, dATP, dGTP, dTTP
  100 µg/mL acetylated bovine serum albumin
  6 mM $MgCl_2$
  50 nM primer/target complex (SEQ ID NO:15 and SEQ ID NO:13 complementary strand)
  16 units BsoBI
  4 units Bca polymerase
  0.01 mCi α-$^{32}$P-dATP The reaction mixtures (minus the enzymes) were heated for 3 minutes to denature the target DNA and cooled to the desired temperature for amplification to anneal the primers (40° C. for HincII and 60° C. for BsoBI). After equilibrating for 3 minutes, 2 µL of polymerase were added and the extension reaction was allowed to proceed for 20 minutes to produce a completely double stranded target 85 nucleotides in length for the HincII system and 103 nucleotides in length for the BsoBI systems. A 3.5 µL aliquot was then removed to 5 µL of stop solution as a control for the extension reaction. The appropriate restriction endonuclease was then added (2 µL). For HincII, time points were taken at 5, 20 and 60 minutes. For BsoBI, time points were taken at 1, 3, and 6 minutes. Aliquots for each time point were added directly to 5 µL of stop solution. The samples were then heated by boiling for 2 minutes and 5 µL were loaded for electrophoresis on a denaturing polyacrylamide gel. The gels were analyzed by autoradiography.

The expected reaction products for the HincII conventional SDA reaction were the full length, intact target molecule (85 nucleotides in length) and a nicked, displaced amplification product 60 nucleotides in length. The expected products for the BsoBI reactions were the full length target (103 nucleotides in length) and an 81-mer amplification product. All of these products were detected. However, there was a marked difference in reaction rates between the conventional HincII/exo⁻ klenow system and the BsoBI/Bca system. The HincII reaction required approximately 60 minutes to generate a detectable level of nicked, diplaced amplification products. In contrast, the BsoBI system required only about 6 minutes to generate detectable levels of target sequence amplification. Of the two reaction conditions tested for the BsoBI system, Reaction Condition C with a lower concentration of $MgCl_2$ produced an improved rate of amplification as compared to Reaction Condition B.

---

What is claimed is:

1. A method for amplifying a target sequence comprising:
A) providing a single stranded nucleic acid fragment containing the target sequence, the fragment having a 5' end and a 3' end;
B) binding an amplification primer for SDA to the 3' end of the fragment such that the primer forms a 5' single stranded overhang, the amplification primer comprising a recognition/cleavage site for a thermophilic restriction endonuclease which does not cut the target nucleic acid sequence, and;
C) amplifying the target sequence at 50° C.–60° C. in a reaction comprising the steps of
i) extending the amplification primer on the fragment in the presence of
a) a thermophilic DNA polymerase having a temperature optimum for polymerizing activity of 65° C.–75° C., the polymerase having strand displacing activity and lacking 5'-3' exonuclease activity,
b) deoxynucleoside triphosphates,
c) at least one derivatized deoxynucleoside triphosphate, and
d) a thermophilic restriction endonuclease which nicks the recognition/cleavage site when the site is hemimodified by incorporation of the derivatized deoxynucleoside triphosphate, the endonuclease having a temperature optimum for cleavage of double-stranded DNA of 50° C.–65° C.,
thereby producing a first double stranded product comprising the amplification primer, a first newly synthesized strand complementary to the target sequence, and a double stranded hemimodified restriction endonuclease recognition/cleavage site;
ii) nicking the double stranded hemimodified restriction endonuclease recognition/cleavage site with the restriction endonuclease;
iii) extending from the nick using the DNA polymerase, thereby displacing the first newly synthesized strand from the fragment and generating a second extension product comprising a second newly synthesized strand, and;
iv) repeating the nicking, extending and displacing steps such that the target sequence is amplified.

2. A method for amplifying a target sequence comprising:
A) providing a first single stranded fragment comprising the target sequence and a second single stranded fragment complementary thereto, the first and second single stranded fragments each having a 5' end and a 3' end;
B) binding a first amplification primer for SDA to the 3' end of the first single stranded fragment and a second amplification primer for SDA to the 3' end of the second single stranded fragment such that the first and second amplification primers form 5' single stranded overhangs on the first and second single stranded fragments, respectively, the first and second amplification primers each comprising a 5' end comprising a recognition/cleavage site for a thermophilic restriction endonuclease which does not cut the target nucleic acid sequence, and;
C) amplifying the target sequence at 50° C.–60° C. in a reaction comprising the steps of
i) extending the first and second amplification primers on the first and second single stranded fragments, respectively, in the presence of
a) a thermophilic DNA polymerase having an optimum temperature for polymerization of 65° C.–75° C., the polymerase having strand displacing activity and lacking 5'-3' exonuclease activity,
b) deoxynucleoside triphosphates,
c) at least one substituted deoxynucleoside triphosphate, and
d) a thermophilic restriction endonuclease which nicks the recognition/cleavage site when the site is hemimodified by incorporation of the substituted deoxynucleoside triphosphate, the endonuclease having an optimum temperature for cleavage of double-stranded DNA of 50° C.–65° C., thereby producing a first and a second double stranded product, the first double stranded product comprising the first amplification primer, a first newly synthesized strand complementary to the first single stranded fragment and a first double stranded hemimodified restriction endonuclease recognition sequence, and the second double stranded product comprising the second amplification primer, a second newly synthesized strand complementary to the second single stranded fragment and a second double stranded hemimodified restriction endonuclease recognition/cleavage site;

ii) nicking the first and second hemimodified restriction endonuclease recognition/cleavage sites with the thermophilic restriction endonuclease;

iii) extending from the nicks using the DNA polymerase, thereby displacing the first newly synthesized strand from the first single stranded fragment and displacing the second newly synthesized strand from the second single stranded fragment, thereby producing a third and a fourth newly synthesized strand, respectively;

iv) repeating the nicking, extending and displacing steps such that the target sequence is amplified.

3. A method for amplifying a target sequence comprising:

A) binding an amplification primer for SDA 3' to the target sequence on a single stranded nucleic acid fragment comprising the target sequence, the amplification primer comprising a recognition/cleavage site for a thermophilic restriction endonuclease which does not cut the target nucleic acid sequence, and;

B) amplifying the target sequence at 50° C.–60° C. in a reaction comprising the steps of i) extending the amplification primer on the fragment in the presence of a) a thermophilic DNA polymerase having an optimum temperature for polymerizing activity of 65° C.–75° C., the polymerase having strand displacing activity and lacking 5'-3' exonuclease activity, deoxynucleoside triphosphates, b) at least one substituted deoxynucleoside triphosphate, and c) a thermophilic restriction endonuclease which nicks the recognition/cleavage site when the site is hemimodified by incorporation of the substituted deoxynucleoside triphosphate, the endonuclease having an optimum temperature for cleavage of double-stranded DNA of 50° C.–65° C., thereby producing a first extension product of the amplification primer comprising a first newly synthesized strand;

ii) displacing the first extension product from the fragment;

iii) synthesizing a complementary strand for the first extension product in the presence of at least one of the substituted deoxynucleoside triphosphates, thereby generating a double stranded hemimodified restriction endonuclease recognition/cleavage site;

iv) nicking the double stranded hemimodified restriction endonuclease recognition/cleavage site with the thermophilic restriction endonuclease;

v) extending from the nick using the polymerase, thereby displacing the first newly synthesized strand from the fragment and generating a second extension product comprising a second newly synthesized strand, and;

vi) repeating the nicking, extending and displacing steps such that the target sequence is amplified.

4. A method for amplifying a target sequence comprising:

A) providing a single-stranded nucleic acid containing the target sequence, the single-stranded nucleic acid having a 5' end and a 3' end;

B) binding an amplification primer for SDA to the 3' end of the single-stranded nucleic acid such that the primer forms a 5' single stranded overhang, the amplification primer comprising a recognition/cleavage site for a thermophilic restriction endonuclease which does not cut the target nucleic acid sequence, and;

C) amplifying the target sequence at 50° C.–60° C. in a reaction comprising the steps of i) extending the amplification primer on the fragment in the presence of a) a thermophilic DNA polymerase having a temperature optimum for polymerizing activity of 65° C.–75° C., the polymerase having strand displacing activity and lacking 5'-3' exonuclease activity, deoxynucleoside triphosphates, b) at least one derivatized deoxynucleoside triphosphate, and c) a thermophilic restriction endonuclease which nicks the recognition/cleavage site when the site is hemimodified by incorporation of the derivatized deoxynucleoside triphosphate, the endonuclease having a temperature optimum for cleavage of double-stranded DNA of 50° C.–65° C., thereby producing a double-stranded product comprising the single-stranded nucleic acid, an extension product complementary to the single-stranded nucleic acid and a double-stranded hemimodified restriction endonuclease recognition/cleavage site consisting of an unmodified primer strand and a complementary modified strand;

ii) nicking the modified strand of the double stranded hemimodified restriction endonuclease recognition/cleavage site with the restriction endonuclease;

iii) extending from the nick using the DNA polymerase, thereby displacing the single-stranded nucleic acid containing the target sequence from the double-stranded product and generating a newly synthesized strand, and;

iv) repeating the nicking, extending and displacing steps such that the target sequence is amplified.

5. The method of claim 2 wherein a double stranded fragment comprising the target sequence is generated by a method comprising:

a) binding the first and second amplification primers to a nucleic acid fragment comprising the target sequence, the first and second amplification primers binding 3' to the target sequence on opposite strands of the nucleic acid fragment;

b) extending the first and secondn amplification primers on the fragment, thereby producing a first extension product of the first amplification primer and a second extension product of the second amplification primer;

b) displacing the first and second extension products by extension of a first and second bumper primer, and;

c) synthesizing complementary strands for the displaced first and second extension products in the presence of the derivatized deoxynucleoside triphosphate, thereby generating double stranded fragments comprising the target sequence which are amplifiable by SDA.

6. The method of claim 5 wherein the DNA polymerase is selected from the group consisting of Bca polymerase and Bst polymerase.

7. The method of claim 6 wherein the thermophilic restriction endonuclease is selected from the group consisting of BsrI, BstNI, BsmAI, BslI, BsoBI and BstOI.

8. The method of claim 3 wherein the DNA polymerase is selected from the group consisting of Bca polymerase and Bst polymerase.

9. The method of claim 8 wherein the thermophilic restriction endonuclease is selected from the group consisting of BsrI, BstNI, BsmAI, BslI, BsoBI and BstOI.

10. The method of claim 1 wherein the amplification primer is extended on the fragment in the presence of dUTP.

11. The method of claim 10 further comprising rendering dU containing DNA unamplifiable by treatment with UDG.

12. The method of claim 11 further comprising inactivation of UDG by treatment with Ugi.

13. The method of claim 2 wherein the first and second amplification primers are extended on the first and second single-stranded fragments in the presence of dUTP.

14. The method of claim 13 further comprising rendering dU containing DNA unamplifiable by treatment with UDG.

15. The method of claim 14 further comprising inactivation of UDG by treatment with Ugi.

16. The method of claim 3 wherein the amplification primer is extended on the fragment in the presence of dUTP.

17. The method of claim 16 further comprising rendering dU containing DNA unamplifiable by treatment with UDG.

18. The method of claim 17 further comprising inactivation of UDG by treatment with Ugi.

* * * * *